United States Patent
Barlos et al.

(10) Patent No.: US 10,711,053 B2
(45) Date of Patent: Jul. 14, 2020

(54) INSULIN LIKE PEPTIDES

(71) Applicant: Chemical & Biopharmaceutical Laboratories of Patras SA, Paralia Patras (GR)

(72) Inventors: Kleomenis Barlos, Patra (GR); Konstantinos Barlos, Patra (GR)

(73) Assignee: CHEMICAL & BIOPHARMACEUTICAL LABORATORIES OF PATRAS SA, Patras (GR)

( * ) Notice: Subject to any disclaimer, the term of this patent is extended or adjusted under 35 U.S.C. 154(b) by 0 days.

(21) Appl. No.: 14/711,494

(22) Filed: May 13, 2015

(65) Prior Publication Data
US 2016/0009778 A1 Jan. 14, 2016

Related U.S. Application Data

(63) Continuation of application No. 13/500,978, filed as application No. PCT/GR2010/000045 on Oct. 8, 2010, now abandoned.

(30) Foreign Application Priority Data

Oct. 8, 2009 (GR) .................. 20090100545

(51) Int. Cl.
| | |
|---|---|
| *A61K 38/28* | (2006.01) |
| *C07K 14/62* | (2006.01) |
| *A61K 38/30* | (2006.01) |
| *C07K 14/65* | (2006.01) |
| *C07K 14/64* | (2006.01) |
| *A61K 38/12* | (2006.01) |
| *A61K 38/16* | (2006.01) |
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C07K 14/82* | (2006.01) |
| *C07K 1/107* | (2006.01) |
| *C07K 1/113* | (2006.01) |

(52) U.S. Cl.
CPC .......... *C07K 14/82* (2013.01); *C07K 1/1075* (2013.01); *C07K 1/1133* (2013.01); *A61K 38/00* (2013.01)

(58) Field of Classification Search
CPC ........ A61K 38/28; A61K 38/30; C07K 14/62; C07K 14/65
See application file for complete search history.

(56) References Cited

U.S. PATENT DOCUMENTS

| 7,893,197 B2* | 2/2011 | Bonaventure .......... C07K 14/62 530/300 |
| 2008/0051336 A1* | 2/2008 | Bonaventure .......... C07K 14/62 514/12.7 |
| 2011/0039778 A1* | 2/2011 | Barlos .................... C07K 14/64 514/12.7 |

FOREIGN PATENT DOCUMENTS

| CN | 1968964 A | 5/2007 |
| CN | 102647996 A | 8/2012 |
| EP | 0 251 615 A2 | 1/1988 |
| EP | 0 945 443 A1 | 9/1999 |
| WO | 2000/027825 A1 | 5/2000 |
| WO | 2001/085700 A1 | 11/2001 |
| WO | 2005/123771 A2 | 12/2005 |
| WO | 2006/094930 A1 | 9/2006 |
| WO | 2007/093220 A1 | 8/2007 |
| WO | 2008/068299 A2 | 6/2008 |
| WO | 2008/071587 A2 | 6/2008 |
| WO | 2010/150279 A2 | 12/2010 |
| WO | 2011/017079 A1 | 2/2011 |

OTHER PUBLICATIONS

Tang et al. "Human Gene 2 Relaxin Chain Combination and Folding" Biochemistry 42:2731-2739, published 2003.*
Haugaard-Jonsson et al. "Structure of the R3/I5 Chimeric Relaxin Peptide, a Selective GPCR135 and GPCR142 Agonist" J. Biol. Chem. 283:23811-23818. Published Aug. 29, 2008.*
Tsetseni et al. "Improvements in the Chemical Synthesis of Insulin-Like Peptides" Peptides for Youth: The Proceedings of the 20th American Peptide Symposium. p. 185-186. Jun. 23, 2009.*
Liu et al. "Relaxin-3/Insulin-Like Peptide 5 Chimeric Peptide, a Selective Ligand for G Protein-Coupled Receptor (GPCR)135 and GPCR142 over Leucine-Rich Repeat-Containing G Protein-Coupled Receptor 7" Molecular Pharmacology 67:231-240. (Year: 2005).*
Barlos et al. "An optimized chemical synthesis of human relaxin-2" J. Peptide Sci. 16:200-211. (Year: 2010).*
Barlos et al. (Feb. 26, 2010) "An optimized chemical synthesis of human relaxin-2" J. Peptide Sci. 16:200-211.
Büllesbach et al. (1991) "Total synthesis of human relaxin and human relaxin derivatives by solid-phase peptide synthesis and site-directed chain combination," J. Biol. Chem. 266(17):10754-10761.
Christensson et al. (2009) "Air oxidation increase skin irritation from fragrance terpenes," Contact Dermatitis. 60(1):32-40.—Abstract Only.
Egdal et al. (2009) "Air oxidation of divanadium (IV) complexes," Dalton Trans. 2009(19):3833-3839—Abstract Only.

(Continued)

*Primary Examiner* — James H Alstrum-Acevedo
*Assistant Examiner* — Zachary J Miknis
(74) *Attorney, Agent, or Firm* — Brian C. Trinque; Lathrop GPM LLP

(57) ABSTRACT

It is described the preparation of Insulin like peptides, of chimeric Insulin like peptides and of their derivatives by the random combination of their chains A and their chains B and the pharmaceutical application of the obtained products.

12 Claims, 9 Drawing Sheets

Specification includes a Sequence Listing.

(56) References Cited

OTHER PUBLICATIONS

Haugaard-Jönsson et al. (2008) "Structure of the R3/I5 Chimeric Relaxin Peptide, a Selective GPCR135 and GPCR142 Agonist," J. Biol. Chem. 283(35):23811-23818.

Liu et al. (2004) "Relaxin-3/Insulin-Like Peptide 5 Chimeric Peptide, a Selective Ligand for G Protein-Coupled Receptor (GPCR)135 and GPCR142 over Leucine-Rich Repeat-Containing G Protein-Coupled Receptor 7," Molecular Pharmacology. 67:231-240.

Ludovici et al. (2001) "Evolution of anti-HIV Drug Candidates. Part 3: Diarylpyrimidine (DAPY) Analogues," Bioorg. Med. Chem. Lett. 11(17):2235-2239.

Maglott et al. (2001) "Engineering disulfide cross-links in RNA via air oxidation," Ch. 5 Unit 5.4 In; Current Protocol Nucleic Acid Chemistry.—Abstract Only.

Rosengren et al. (2009) "Structural Insights into the Function of Relaxins," Annals of NY Academy of Science. 1160:20-26.

Tang et al. (2003) "Human gene 2 relaxin chain combination and folding," Biochemistry. 42(9):2731-2739.

Wade et al. (2009) "The chemical synthesis of relaxin and related peptides," Annals of NY Academy of Science. 160:11-15.

Wang (1999) "Instability, stabilization, and formulation of liquid protein pharmaceuticals," Intl. J. Pharmaceutics. 85:129-188.

International Search Report with Written Opinion corresponding to International Patent Application No. PCT/GR2010/000045, dated Apr. 26, 2011.

Bathgate, et al. (2006) "Relaxin-3: Improved Synthesis Strategy and Demonstration of Its High-Affinity Interaction with the Relaxin Receptor LGR7 Both In Vitro and In Vivo", Biochemistry, 45: 1043-1053.

Bellotti, V. et al., "Protein Misfolding Diseases," The Open Biology Journal, 2009, vol. 2, pp. 228-234.

Sherwood, O.D., "Relaxin's Physiological Roles and Other Diverse Actions," Endocrine Reviews, 2004, vol. 25, No. 2, pp. 205-234.

De Meyts, P. et al., "Insulin and IGF-1 Receptor Structure and Binding Mechanism," Chapter 1 in "Mechanisms of Insulin action" edited by Alan R Saltiel, Jeffrey E Pessin, Springer (2007), 36 pages.

Soto, C., "Protein misfolding and disease; protein refolding and therapy," FEBS Letters, 2001, vol. 498, pp. 204-207.

Wilkinson, T.N. et al., "Evolution of the relaxin-like peptide family," BMC Evolutionary Biology, 2005, vol. 5, p. 14.

* cited by examiner

Figure 1

INSULIN LIKE PEPTIDES

RELATED APPLICATIONS

The present application is a continuation of U.S. patent application Ser. No. 13/500,978, filed Jun. 29, 2012, which claims the benefit of priority of International Application No. PCT/GR2010/000045 filed Oct. 8, 2010, which claims priority to Greek Patent Application No. 20090100545 filed Oct. 8, 2009. The entire contents of each of the above documents are incorporated herein by reference.

Insulin like peptides (INSL) e.g. these peptides with similar structure to insulin, are consisted from two peptide chains the A- and B-chains which are joined together by two intermolecular disulfide bonds, while the A-chain contain an additional intramolecular disulfide bond. An exception are the insulin like growth factors IGF-1 and IGF-2 where each of them is consisted from a single chain peptide containing 70 amino acids.

The family of the INSL contain besides insulin the INSL3, INSL4, INSL5, INSL6, the relaxin 1 (RLN1), relaxin 2 (RLN2) and relaxin 3 (RLN3) as well as the growth factors IGF-1 και IGF-2.

The INSL peptides reveal important biological properties, which determine metabolism such as insulin and IGF-1 and regulate important conditions of the organism such as pregnancy, which is regulated by the RLN1, RLN-2 and INSL4.

Besides insulin which is on the market for the treatment of diabetes and can be considered as the best studied protein, the IGF-1 which is used in the cases for severe primary IGF-1 deficiency and is tested in many clinical trials among others for indications such as type 1 diabetes, type 2 diabetes, Alzheimer, severe burnings and myotonic muscle dystrophy (MMD) and RLN2 which is tested among others in clinical trials for acute heart failure, preeclampsia and sclerodermia, only little is known about the biological properties and possible therapeutic applications of the other INSL their derivatives and their antagonists.

In one case chimeric peptides consisting from the chain A of an INSL and the chain b of another INSL has been shown to be able to interact with distinct receptors of the corresponding INSL and to reveal significant biological activity. In addition it has been shown that IGF where its peptide chain is consisted from the part A of IGF-1 and the part B of IGF-2 has additional important biological activity. The same was proved for a large number of other chimeric peptides.

The biological properties and the possible pharmaceutical applications of chimeric INSL are not investigated in depth because their manufacturing is very difficult. In fact only chimeric peptides which consist from chain B of the INSL5 with various A chains of other INSL have been prepared and investigated. Especially RLN3A/INSL5 consisting from the A chain of RLN3 and of the B chain of INSL5 has been found to interact with the GPCR135 η GPCR142 receptors.

The reason that the cheimeric peptides, which consist of two different chains of INSL, are only limited studied is their difficult and low yielding synthesis.

The methods which have been applied to date are A) the random mixing of the linear A and B chain and their oxidation B) the mixing of A chain which contain sulfonic acid groups at the position of the thiol groups of the cysteine residues and C) the site directed building of the three disulfide bonds between the chains A and B. Until now this method was considered as the most improved chemical method for the preparation of INSL although it requires several steps and five chromatographic purification steps. It is obvious that all above methods not only are unsatisfactory but lead with grate difficulties and high cost to small amounts of INSL. In addition these methods are not suitable for large scale production.

Because of the difficulties of their chemical synthesis the production of these peptides such as for example of insulin, relaxin and IGF is performed utilizing recombinant DNA techniques. But also recombinant DNA techniques are more complicated than the common synthesis of peptide and proteins. So even in the simplest case of IGF-1 it is required after the isolation of the linear chain the selective formation of three disulfide bonds.

It becomes even more difficult in the production of INSL which consist of two peptide chains because in that case the propeptides for example those of proinsulin, prorelaxin etc. are synthesized with recombinant DNA techniques, then the selective formation of the disulfide bonds and finally utilizing enzymes the middle C-peptides of the propeptides are removed.

Even more complicated is the production of RLN2 where for its production an additional step is required after the cleavage of the C-peptide for the conversion of the glutamine residue positioned ate the amino terminus of the A-chain to a pyrroglutamic acid residue by heating. So even the biotechnologically produced INSL are very difficult to produce and many chromatographic purifications are required to obtain them in a pharmaceutically acceptable purity. These big difficulties and the high production cost have lead to the great delay of the evaluation of the biological properties of many INSL and the testing in clinical trials of their pharmaceutical applications this, although their biological activity can be considered as certain. The same is true for the chimeric INSL which contain insulin chains combined with the chains of other INSL.

DESCRIPTION OF INVENTION

Recently we discovered and communicated a simple production method for RLN1 and RLN2 by the random combination of their chains. The method showed that chimeric peptides consisting e.g. by RLN2A/RLN1B are synthesized with great ease. Particularly effective was the method of synthesis where monocyclic and bicyclic chains A were used. This showed that the A chain contains structural information such that enables it to combine with insulin-B peptide chains that do not correspond to the native pair of chains.

In our invention we describe that the structural features of an insulin like peptide A chain allows it to recognize and selectively combine with all the B chains of Insulin and other similar to that peptides. The combination of the chains always gives selectively the corresponding expected and a natural insulin-like combination.

For example the invention show that bicyclic RLN2A recognizes and connects via a random combination not only with the B chains of other INSL but even with chains which theoretically correspond to a B chain of an INSL and correspond to the chain B of the IGF-1 and IGF-2 which are found in nature as a single chain peptide. The same applies to combinations of other insulin-like peptides and gave us the possibility to produce easily chimeric polypeptides with possible pharmaceutical activity.

In our invention it is described that the main side product of the reactions of cyclic and bicyclic A chain is the oxidation of the B-chain to cyclic B-chains. In particular, the reaction of the linear B-chain with bicyclic A chain of INSL A chain is very fast and if the A chain is in excess oxidizes the B chain to cyclic chain B within few minutes in parallel with the formation of the insulin-like peptide.

This property of the bicyclic peptide A to oxidize effectively and to create disulfide bonds links is a property of oxidases and so we can describe the bicyclic A chain of insulin-like peptides as the smallest known and at the same time strong oxidases which show in addition the capacity of the easy combination with other peptide chains.

Exactly this property makes bicyclic A chains of INSL and of similar peptide chains as interesting therapeutics for protein conformational diseases. Thus a protein which folds slowly because of a malfunction of the organism can be helped by providing an appropriate bicyclic INSL A chain or a similar peptide.

We also disclose here that bicyclic A chains of INSL react easily with peptide chains that contain only a cysteine residue which does not participate in disulfide bonds as for example in certain mutations of insulin which lead to diabetes.

The administration of bicyclic A chains as pharmaceuticals will be for this reason extremely beneficial for the clearance of mutant proteins from the human or the animal organism by its combination reaction with mutant protein followed by the destruction of the combination of the bicyclic chain A with the mutated protein by the ERAD system or other defence systems of the organism.

The delivery of the bicyclic A chains as pharmaceuticals will be extremely beneficial because it will react with precipitated proteins and would dissolve them and also with protein oligomers or polymers which would also be dissolved and through of their oxidative activity would be folded restoring thus their functionality.

In another embodiment of our invention we describe an easy and efficient synthesis of peptide chains of INSL by their solid phase synthesis where 2-chlorotrityl and 4-methyl benzydryl resins are used. For the preparation of linear peptides or peptide amides all techniques known in the art can be used in addition.

The present invention describes an improved chemical synthesis of known INSL and of chimeric peptides. There are also described for the first time chimeric derivatives of IGF-1 and IGF-2 which consist of two chains (FIG. 1) and the chains are linked in the manner of the linkage of the chains of insulin and of other insulin-like peptides. Also described for the first time is a series of chimeric INSL consisting of an A chain of an INSL and the B-chain of another INSL.

Very important for peptide synthesis of INSL is the correct formation of the disulfide links. In the present invention we describe a method of formation of the correct —S—S-combinations. These oxidation reactions of cysteine residues can be made before or after the purification of the individual chains. Also the formation of disulfide/s links can be achieved by peptides in their protected form.

If the synthesis of the two chains is performed on solid-phase the formation of the disulfide bond can be created on the resin, after cleaving the peptide from the resin or simultaneously with its cleavage from the resin. The oxidation of cysteine thiol functions for the formation of intramolecular disulfide bonds can be performed using any oxidant but preferably with dimethyl sulfoxide (DMSO) (J P Tam, et all. J. Am. Chem. Soc. 1991, 113, 6657-6662) on deprotected INSL chains and with iodine where the oxidation takes place with protected or partially deprotected peptides.

For the protection of the side-chain cysteine thiol groups during the assembly of the chains each protecting group known in the scientific field of the protection of the thiol functions can be used but preferably 4-methoxytrityl (Mmt) (Barlos et all. Int. J. Peptide Protein Res. 1996, 47, 148-153), the trityl (Trt)] and aketamidomethyl (Acm) groups.

We also describe in our invention that an increase in solubility of A and B chains of insulin-like peptides is achieved by their oxidation to the corresponding bicyclic and monocyclic A and B chains. So they are eluted much earlier in preparative high-performance liquid chromatography (HPLC) than the corresponding (reduced) peptides their application for purification is simple and superior over the application of linear (reduced) peptides.

For the selective formation of intermolecular disulfide bonds in the A chain any pair of orthogonal protecting groups can be used but preferred is the use of one of the pairs Trt/Mmt, Trt/Acm and Mmt/Acm.

When using the Trt/Mmt pair the S-Mmt group is removed selectively followed by the formation of the disulfide bond between the liberated thiol functions by oxidation with a suitable oxidant, preferably with air or DMSO. Preferably the second disulfide bond is formed by oxidative removal of the S-Trt and S-Acm groups with iodine. Using 2-chlorotrityl resin (K. Barlos et all, Int. J. Pept. Protein Res. 1991, 37, 513-520), or a resin with a similar sensitivity to acids for the solid-phase synthesis of A-chains, the selective removal of the S-Mmt groups with mild cleavage with acids is performed simultaneously with the cleavage of the peptide from the resin.

For the oxidative removal of the S-Trt-group which is followed by the formation of disulfide bond any oxidant known in the art can be used but preferably iodine.

If the Trt/Acm pair is used the S-Trt group is removed selectively in the presence of the S-Acm group by acid treatment of the peptide resin with a suitable acid solution preferably with trifluoroacetic acid in dichloromethane at a concentration of 10-100% and adding scavengers, preferably thiol, silanes and water in varying proportions. The formation of the first disulfide bond is effected by oxidation with any oxidant known in the art but preferably DMSO and air.

The formation of the first disulfide bond can be achieved using iodine for the oxidative removal of the S-Trt-groups. This can be done before, during or after the cleavage of the protected peptide from the resin (K. Barlos et all, Int. J. of Peptide & Protein Research, 1991, 38, 562-568).

The required disulfide bond is formed selectively in the presence of S-Acm group if the iodination reaction takes place at low temperatures 0° C.-15° C. in lypophilic solvents, preferably chlorinated hydrocarbons, fluorinated alcohols, mild acids such as acetic acid and trifluoroacetic acid.

The creation of the second disulfide bond is achieved in more polar solvents by adding polar components such as acetic acid, methyl alcohol, trifluoroacetic acid and occasionally water. The temperature during iodolysis may vary but preferably is set in the range of 5-25° C.

The solid phase synthesis of insulin-like peptides may be performed with the application of any known in the scientific field resin but preferably on trityl type resins such as the 2-chlorotrityl resin (K. Barlos, et al., Tetrahedron Lett., 1989, 30, 3943; K. Barlos, et al., Tetrahedron Lett., 1989, 30, 3947; K. Barlos, et al., Angew. Chem. Int. Ed. Engl., 1991, 30, 590; K. Barlos, et al., Int. J. Pept. Protein Res., 1991, 37, 513; K. Barlos, et al., Int. J. Pept. Protein Res., 1991, 38, 562) and 4-methylbenzydryl bromide resin (K. Barlos et all, Liebigs Annalen der Chemie (1989), (10), 951-5).

In our invention we describe improved methods for the combination (folding) of A and B chains of insulin-like peptides (FIGS. 3-9). In general cyclic peptides containing intramolecular disulfide bonds react faster than the corresponding linear peptides during the formation of intermolecular-SS-bonds. They behave such as activated cyclic peptides and perform the intermolecular combination with the second chain with a more effective manner. Peptides with a linear chain are oxidized with DMSO, air or other oxidizing agents in mixtures which contain a mixture of A isomers and a B-chain. In our invention is described that mixtures of bicyclic isomers of the A-chain or each of them individually, react with cyclic beta-chains (FIG. 6) catalytically to the requested products. The reaction is accelerated by the addition of reducing catalysts. The catalyst reduces disulfide bridges into free thiols, thus creating equilibrium of cyclic and intermolecularly joined peptides. This leads with sequential reactions to the thermodynamically more stable products, which are the native proteins.

As the reducing agent can be used any organic or inorganic material, but preferably organic thiols such as the reduced (linear) chain A and/or B reduced glutathione, cysteine, thiophenols, pyridinthiol, 3 or 5 nitropyridin-2-thiol, benzylmercaptane, dithiothreitol, etc. Preferably chain A or B or mixtures thereof are used as catalysts. The catalyst may be added before, during or after the mixing of A and B-chains.

The catalyst can be added in different quantities to create the equilibrium. The temperature during the folding may vary but preferably it is set at 24° C. As the solvent water or mixtures of water with organic solvents are used with the occasional addition of bases. The pH of the combination of the chains can vary but preferably is set at 10-11.

We also show in our invention that reduced chains A combine (fold) with B-chains to insulin-like peptides in the presence of appropriate oxidants such as DMSO. The reactions proceed through the formation of mixtures of monocyclic and bicyclic A-chains.

The combination of the chains is faster when already oxidized A and B-chains are used. In this case, mixtures A and B chains react by giving in all cases the insulin-like peptides with the physical arrangement of their disulfide bonds.

Preferably the combination of bicyclic A-chain with reduced (linear) B-chain (FIG. 4) is performed by adding 15% DMSO as the oxidant to complete the folding. The proportion of A and B-chains may vary but preferably is in Mol 1.1:1. The speed of the reaction increases with increasing the excess of the A-chain in the reaction. In this case the excess of A or B chains is recycled during the HPLC purification of the insulin-like peptides The purification of insulin-like peptides is performed by HPLC using various mixtures of solvents but preferably in water and acetonitrile containing trifluoroacetic acid (TFA), formic acid or acetic acid.

The purified insulin-like peptide can be isolated by freeze-drying or precipitation. If it is required a desalting is performed by usual strong ion exchange resins for example of Dowex.

EXAMPLES

Example 1

Solid-Phase Synthesis of Insulin Like Peptide A Chain, B Chain and of their Protected Segments. General Procedure A1. Preparation of Loaded 2-Chlorotrityl Resins, General Procedure 2-Chlorotrityl chloride resin (CTC-Cl) (100 g; loading 1.6 mmol/g) of CBL-Patras, is placed in a 2 L peptide synthesis reactor and is swollen with 700 mL dichloromethane (DCM) for 30 min at 25° C. The resin is filtered and a solution of 100 mmol Fmoc-amino acid and 300 mmol diisopropylethylamine (DIEA) in 500 mL DCM is added. The mixture is stirred under nitrogen for 2 hours at 25° C. Then, the remaining active sites of 2-CTC resin are neutralised by adding 10 mL of methanol (MeOH) and reacting for 1 hour. The resin is filtered and washed twice with 400 mL DMF. The resin is filtered and treated twice with 500 mL 25% by volume of piperidine in DMF for 30 min. The resin is then washed four times with 500 mL DMF. The resin is diswelled with 3 washes with 500 mL of isopropanol (IPA). The resin is dried to constant weight. On the resin was bound the 70-95% of the mmol of the used amino acid.

A2. Preparation of Loaded MBH-Resins, a General Method

MBH-Br resin (100 g; 190 mmol) was placed in a 2 L peptide synthesizer and swollen with 700 mL DCM for 30 min at 25° C. The resin was filtered and then a solution of Fmoc-amino acid and DIEA in 500 mL DCM was added. The mixture was stirred under nitrogen for 6 h at 25° C. Then the remaining active sites of the MBH resin were bound by adding 10 mL MeOH and stirring for 24 h. The resin was then filtered and washed twice with 400 mL DMF. The resin was filtered and reacted twice with 500 mL of a solution of 25% by volume of piperidine in DMF for 30 min. The resin was then washed four times with 500 mL DMF. The resin was diswelled with three washes with 500 mL IPA. The resin was then dried to constant weight under vacuum (15 torr, 25° C.). 60-90% of the mmol of the used amino acid were bound onto the resin.

B. Solid-Phase Synthesis, a General Protocol

The solid-phase synthesis was performed at 24° C., with 1.0 g amino acid esterified to the CTC or MBH resin as described in Part A of Example 1. During the whole synthesis the following protocol was used.

B1. Swelling of the Resin

The resin was placed in a 15 ml reactor and treated twice with 7 mL NMP, followed by filtration.

B2. Activation of the Amino Acid

The amino acid (3.0 equiv.) and 1-hydroxybenzotriazol (4.0 equiv.) was weighted and dissolved in a reactor with 2.5 their volume in NMP and cooled to 0° C. DIC was then added (3.0 equiv.) and the mixture was stirred for 15 min.

B3. Coupling

The solution which was prepared in B2 was then added to the B1 reactor. The reactor was washed once with one volume of DCM and was added to the reactor which was stirred for 1-3 h at 25°-30° C. In a sample the Kaiser Test was performed to determine the completion of the reaction. If the coupling reaction was not completed after 3 h (positive Kaiser Test), the reaction mixture was filtered and recoupled with a fresh solution of activated amino acid. After completion of the coupling the reaction mixture was filtered and washed 4 times with NMP (5 volumes per wash).

B4. Removal of the Fmoc-Group

The resulting resin in B3 was filtered and then treated for 30 min with 5 mL of a solution which contained 25% by volume of piperidine. The resin is then washed three times with 5 mL NMP.

B5. Elongation of the Peptide Chain

After the incorporation of each amino acid the steps B1-B5 were repeated until the completion of the peptide chain.

For the introduction of each individual amino acid the following Fmoc-amino acids were used: Fmoc-Gly-OH, Fmoc-Ala-OH, Fmoc-Val-OH, Fmoc-Ile-OH, Fmoc-Leu-OH, Fmoc-Met-OH, Fmoc-Met (O)—OH, Fmoc-Phe-OH, Fmoc-Pro-OH, Fmoc-Asp(tBu)-OH, Fmoc-Glu(tBu)-OH, pGlu, Fmoc-Lys(Boc)-OH, Fmoc-Ser(tBu)-OH, Fmoc-Ser(Trt)-OH, Fmoc-Thr(tBu)-OH, Fmoc-Thr(Trt)-OH, Fmoc-Tyr(tBu)-OH, Fmoc-Tyr(Clt)-OH, Fmoc-Asn-OH, Fmoc-Asn(Trt)-OH, Fmoc-Gln-OH, Fmoc-Gln(Trt)-OH, Fmoc-Trp-OH, Fmoc-Trp(Boc)-OH, Fmoc-Arg(Pbf)-OH, Fmoc-His(Trt)-OH, Fmoc-Cys(Trt)-OH, Fmoc-Cys(Mmt)-OH and Fmoc-Cys(Acm)-OH and the following Boc-amino acids: Boc-Arg(Pbf)-OH, Boc-Gln-OH, Boc-Gln (Trt)-OH, Boc-Lys(Boc)-OH and Boc-Asp(tBu)-OH.

C. General Method for the Cleavage from the CTC-Resin of the Insulin Like Peptides and of their Protected Segments which Contain Fmoc- or Boc-Groups on their N-Terminus.

The resin-bound peptide or peptide segment which was produced as described above in B1-B5 was washed 4 times with 5 mL NMP, 3 times with 5 ml IPA and finally 5 times with 7 ml DCM to remove completely any residual NMP or other basic components. The resin was then cooled to 0° C., filtered from DCM and was treated twice with a solution of 10 mL 1% TFA/DCM at 5° C. The mixture is then stirred 20 min at 0° C. and filtered. The resin is then washed three times with 10 mL DCM. Pyridine is then added to the filtrates (1.3 equiv. relative to TFA) to neutralize the TFA. The cleavage solution in DCM is then mixed with an equal volume of water. The resulting mixture is distilled at reduced pressure to remove DCM (350 torr at 28° C.). The peptide or peptide segment precipitated after the removal of DCM. The resulting peptide is washed then with water and dried at 30-35° C. under 15 Torr vacuum.

Example 2

Deprotection of the Insulin Like Peptides. General Method

The protected chains A and B obtained as described above in Example 1 (0.01 mmol) are treated with 10 mL TFA/DTT/water (90:5:5) for 3 h at 5° C. and for 1 h at 15° C. The resulting solution is concentrated in vacuum and then the deprotected peptide was precipitated by the addition of diisopropylether and washed three times with 10 mL diisopropylether. The resulting solid was dried in vacuum (25° C., 15 Torr) until constant weight.

Example 3

Deprotection of Mono and Bicyclic Insulin Like Peptides. General Method

The protected RLX-chains A and B which were obtained as described above in the example 1 (0.05 mmol) were treated with 5 mL of a mixture of TFA/TIPS/anisole/water (91:4:1:4) for three h at 5° C. and for 1 h at 15° C. The resulting solution is concentrated in a vacuum and the deprotected peptide was then precipitated by the addition of diisopropylether and washed three times with 10 mL diisopropylether. The resulting solid material was dried in vacuum (25° C., 15 Torr) until constant weight. The procedure was repeated for each of the chains A and B.

Example 4

Purification of the Deprotected Peptides and of their Monocyclic and Bicyclic Derivatives. General Procedure Crude deprotected trifluoroacetic acid salts of RLX1A, RLX2A, Met24 (O)-RLX1B and Met25 (O)-RLX2B and mono- and bicyclic derivatives were dissolved in 25% acetonitrile in water and loaded on a semipreparative column 10×25 mm Lichrospher 1.00, RP-18, 12 micron (Merck); Phase A=1%-TFA in acetonitrile, phase B=1%-TFA in water; Linear gradient from 25%-A to 65%-A in 30 min. The purification yield vary from 30 to 80%. The process was repeated for RLX2A, Met24 (O)-RLX1B and Met25 (O)-RLX2B and for the mono and dioxidized derivatives.

Example 5

Cleavage from the CTC-Resin and Simultaneous Monooxidation of Protected Peptides with Iodine. Preparation of Monooxidized A and B-Chains of Insulin Like Peptides The resin bound on the N- and on the side chains protected peptide, obtained as described above in the examples 1 and 2 was washed 4 times with 5 mL NMP, 3 times with 5 ml IPA and finally 5 times with 7 ml DCM to remove completely NMP and other basic components. The resin is then cooled to 0° C. After filtration of DCM the resin is processed twice at 5° C. with a solution of 10 mL 1%-TFA in DCM containing 10 equivalents (equiv.) of iodine in relation to the on the resin bound peptide. The resulting mixture is stirred for 5 min at 0° C. and filter (instead of 1% TFA the same volume of a mixture of dichloromethane/acetic acid/trifthoroethanol can be used with similar results). The resin is then washed three times with 10 mL DCM. The combined filtrates are heated to 15° C. and stirred for further 30 min. Pyridine is then added to the filtrates (1.3 equiv. relative to TFA) to neutralize TFA. The cleavage solution in DCM is then mixed with an equal volume of 3%-sodium thiosulphate in water in order to remove the excess iodine. This is indicated by the discoloration of the mixture. The resulting mixture is distilled at low pressure to remove DCM (350 torr at 28° C.). The resulting peptide or peptide segment precipitated out after the removal of DCM. The resulting peptide was washed with water and dried at 30-35° C. under vacuum of 15 Torr. Deprotection and purification were performed as described in the examples 2, 3 and 4. The overall yield vary at 45-65%. The process was repeated for all molecules.

Example 6

Synthesis of Protected Monocyclic Insulin Like Peptides by Oxidation with DMSO. General Method A.1. Selective Deprotection of Cys(Mmt). Partial Deprotection of Insulin Like Peptides.

The resin bound on the N- and at the side chains protected peptide obtained as described above in the examples B1-B5 (0.005 mmol) and which contains two protected cysteine residues with Trt and two protected cysteine residues with Mint is washed 4 times with 5 mL NMP, 3 times with 5 ml IPA and finally 5 times with 7 ml DCM to remove completely the NMP and other basic components. The resin is then cooled to 0° C., DCM was filtered and the resin was treated four times with a solution of 25 mL 1.5%-TFA in DCM at 5° C. which contained 10 equivalents of triethylsilane in relation to the resin linked peptide. The combined filtrates were stirred for additional 2 h at 15° C. Pyridine is then added to the filtrates (1.3 equiv. relative to TFA) to remove the TFA. The resulting cleavage solution in DCM was then mixed with an equal volume of water. The resulting mixture is distilled at low pressure to remove DCM (350 torr at 28° C.). The selectively at S-Mmt partially deprotected peptide or peptide segment precipitated out after the removal of DCM. The resulting peptide was then washed with water and dried at 30-35° C. under vacuum 15 Torr.

A2. Oxidation with DMSO from a Free Cysteine to Monocyclic.

The peptides that were obtained as described in the A1 method (0.005 mmol) were dissolved in 5 ml DMSO and stirred for 24 hours at 25° C. Then 5 ml of water were added and the stirring was continued for additional 30 min. The precipitated monocyclic protected peptide was then washed five times with water and was dried in vacuum to constant weight (30° C., 15 Torr). Deprotection and purification were performed as described in the examples 2, 3 and 4. The overall yield is in the range of 50 to 70%.

Example 7

Synthesis of Bicyclic a Chains of Insulin Like Peptides and their Derivatives, General Method A1. Oxidation with Iodine of Protected Monocyclic A Chains of Insulin-Like Peptides and their Derivatives, in which Two Cys Residues are Protected at their Side Chains with Trt-Groups.

Monocyclic protected A chains of insulin-like peptides and their derivatives, (0.005 mmol) in which two Cys residues are side chain protected with Trt-groups were dissolved in 5 ml DCM/TFE (7:3). The solution is cooled to 5° C. and then 10 equiv. Iodine in 5 ml DCM were added and the mixture was stirred for 1 h. The cleavage solution in DCM was then mixed with an equal volume of 3%-sodium thiosulphate in water to remove the excess iodine. This is indicated by the discoloration of the mixture. The resulting mixture is distilled at low pressure to remove DCM (350 torr at 28° C.). The resulting peptide or peptide segment precipitated out after the removal of DCM. The resulting peptide precipitated out and was washed with water and dried at 30-35° C. under vacuum of 15 Torr. Deprotection and purification were performed as described in examples 2, 3 and 4. The overall yield varies in the range of 50-80%.

A2. Oxidation with Iodine Protected Monocyclic Monocyclic A Chains of Insulin-Like Peptides and their Derivatives in which Two Cys Side is Protected by Acm-Groups.

Monocyclic protected A chains of insulin-like peptides and of their derivatives (0.005 mmol) in which two Cys residues are side chain protected with Acm-groups were dissolved in 5 ml of AcOH/TFE (5:5). The solution is then cooled at 5° C. and then 20 equiv. iodine in 5 ml TFE were added and the mixture was stirred for 1 h. The cleavage solution in DCM was then mixed with five volumes of 3%-sodium thiosulphate and ascorbic acid in water to remove the excess of iodine. This is indicated by the discoloration of the mixture. The resulting mixture is distilled at low pressure to remove DCM (350 torr at 28° C.). The resulting peptide or peptide segment precipitated out after the removal of DCM and was then washed with water and dried at 30-35° C. under vacuum at 15 Torr. Deprotection and purification were performed as described in the examples 2, 3 and 4. The overall yields vary in the range of 50-60%.

A3. Oxidation with DMSO of Deprotected Monocyclic A Chains of Insulin-Like Peptides and their Derivatives, General Method.

Monocyclic deprotected A chains of insulin-like peptides and their derivatives (0.005 mmol) were dissolved in 4 ml ammonium acetate buffer solution with pH=4. Then 1 ml DMSO was added and the mixture was stirred at 15° C. for 24 h. From the resulting solution the bicyclic peptides were isolated and purified as described in Example 4. The overall yield ranges from 65 to 85%.

A4. Oxidation with DMSO of Linear Deprotected Monocyclic A Chains of Insulin-Like Peptides and their Derivatives, General Method.

Linear deprotected monocyclic A chains of insulin-like peptides and their derivatives (0.005 mmol) were dissolved in 4 ml ammonium acetate buffer solution with pH=4. Then 1 ml DMSO was added and the mixture was stirred at 15° C. for 24 h. From the resulting solution the bicyclic peptides were isolated and purified as described in Example 4. The overall yield ranges from 60-80%.

Example 8

Synthesis of Monocyclics B-Chain of Insulin Like Peptides and Derivatives. General Method Linear deprotected B-chains of insulin-like peptides and of their derivatives (0.005 mmol) were dissolved in 4 ml buffered solution of sodium glycinate with pH=10.5. Then 1 ml DMSO was added and the mixture was stirred at 15° C. for 24 h. From the resulting solution, the cyclic peptides were isolated and cleaned as described in Example 4. The average yield of three experiments was 25-45%.

Example 9

Synthesis of Insulin Like Peptides and their Derivatives by the Linear Combination of the A-Chain of the Insulin Like Peptides and of the Linear B-Chain of Insulin Like Peptides and their Derivatives, General Method Deprotected linear A-chain of insulin like peptides (0.006 mmol) and linear B-chain of insulin like peptides (0.005 mmol) were dissolved in 4 ml buffered solution of sodium glykinate/6-N guanidine hydrochloride (4:1) with pH=10.5. Then 1 ml DMSO was added within 12 hours and then the mixture was stirred for additional 4 h at 15° C. From the resulting solution, the insulin-like peptides were isolated by purifying them as described in Example 4. The average yield of three experiments gave the insulin like peptides in 15-35%.

Example 10

Synthesis of Insulin Like Peptides and their Derivatives by the Linear Combination of the Linear A-Chain of the Insulin Like Peptides and of the Cyclic B-Chain of the Insulin Like Peptides and of their Derivatives, General Method A linear chain Deprotected of insulin like or peptide derivatives (0.005 mmol) and cyclic peptide insulin B chain or derivatives (0.005 mmol) dissolved in 4 ml buffered salt solution glykinis/6-N of guanidine hydrochloride (4:1) at pH=10.5. Then added 1 ml DMSO at 12 hours and then the mixture was stirred for additional 4 h at 15° C. From the resulting solution, the insulin-like peptides were isolated by etching as described in Example 4. The average yield of three experiments were insulin-like peptides 5-70% calculated on used, B-chain.

Example 11

Synthesis Insulin-Derived Peptides and their Combination Monocyclics A Chain of Insulin-Like Peptides and their Derivatives in a Linear Chain of Insulin-B Peptide and Derivatives, a General Method Deprotected monocyclic of insulin like A chain peptide or producer (0.006 mmol) and cyclic peptide chain B of insulin like or producer (0.005 mmol) dissolved in 4 ml buffered salt solution glykinis/6-N of guanidine hydrochloride (4:1) at pH=10.5. Then 1 ml DMSO was added gradually to 12 hours and then the mixture was stirred for additional 4 h at 15° C. From the resulting solution, the insulin-like peptides were isolated by etching as described in Example 4. The average yield of three experiments were insulin-like peptide 12-36% used, calculated on the B-chain.

Example 12

Synthesis of Insulin Like Peptides and of their Derivatives by the Combination of the Monocyclic A-Chain of the Insulin Like Peptides with the Linear B-Chain of the Insulin Like Peptides and of their Derivatives, General Method Deprotected monocyclic A chain of an insulin like peptide or of its derivative (0.006 mmol) and of cyclic B-chain of an insulin like peptide or of its derivative (0.005 mmol) were dissolved in 4 ml buffered solution of sodium glykinate/6-N guanidine hydrochloride (4:1) at pH=10.5. Then 1 ml DMSO was added gradually within 12 hours and then the mixture was stirred for additional 4 h at 15° C. From the resulting solution, the insulin-like peptides were isolated by purifying them as described in the Example 4. The average yield of three experiments were on insulin-like peptide 10-40%, calculated on the applied B-chain.

Example 13

Synthesis of Insulin Like Peptides and of their Derivatives by the Linear Combination of the Bicyclic A-Chain of the Insulin Like Peptides and of its Derivatives and of the Linear B-Chain of Insulin Like Peptides and of their Derivatives, General Method Deprotected bicyclic A-chain of insulin like peptide or of its derivatives (0.006 mmol) and of linear chain-B of insulin like peptides or derivatives (0.005 mmol) dissolved in 4 ml of a buffer of sodium glycinate/6-N guanidine hydrochloride (4:1) at pH=10.5. Then 1 ml DMSO was added gradually within 12 hours and then the mixture was stirred for additional 4 h at 15° C. From the resulting solution, the insulin-like peptides were isolated by purification performed as described in Example 4. The average yield of three experiments on insulin-like peptides was 5-80% calculated on the applied B-chain.

Example 14

Synthesis of Insulin Like Peptides and of their Derivatives by the Combination of the Bicyclic A-Chain of the Insulin Like Peptides and of its Derivatives and of the Cyclic B-Chain of Insulin Like Peptides and of their Derivatives, General Method Deprotected bicyclic A-chain of an insulin like peptide or of its derivatives (0.011 mmol) and cyclic B-chain of an insulin like peptide or its derivatives (0.01 mmol) were dissolved in 15 ml buffer of a solution of sodium glykinate/ 6-N guanidine hydrochloride (4:1) at pH=10.5. Then a solution of 0.4 mmol dithiothreitol in 5 mL water was added over 48 under stirring at 5-10° C. From the resulting solution, the insulin-like peptides were isolated by purification as described in Example 4. The average yield of three experiments on insulin-like peptides was 20-75%, calculated on the applied B-chain.

DESCRIPTION OF FIGURES

Figure 1:
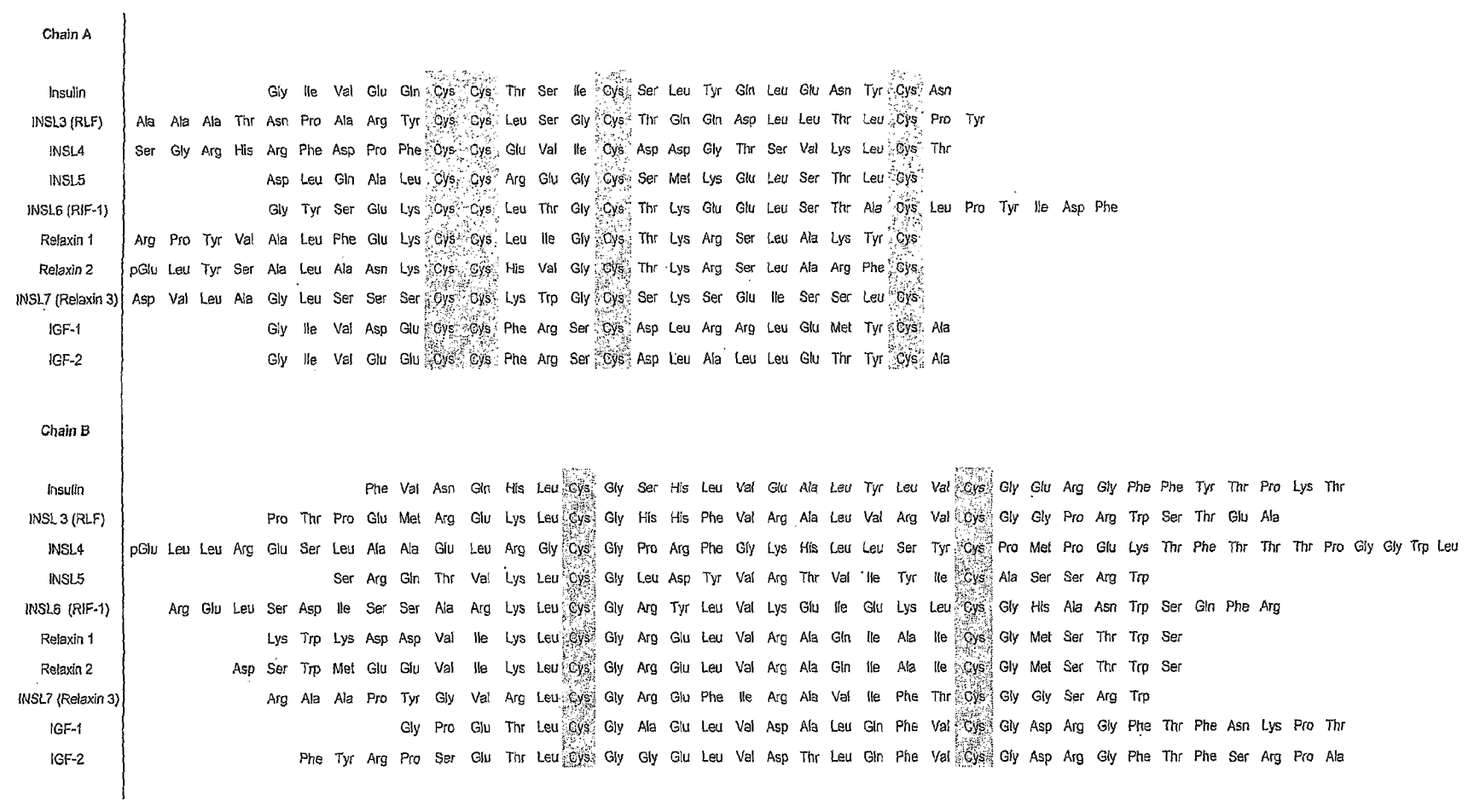

FIG. 1. Primary structure of insulin-like peptides. With shadow are indicated the cysteine residues which are joined together as schematically indicated in FIG. 2. The first cysteine from the N-terminus of the A-chain is joined with the third cysteine from the N terminus of the A chain; the second cysteine from the N-terminus of the A-chain is joined with the first cysteine from the N-terminus of the B chain; the fourth cysteine from the N-terminus of the A-chain is joined with the second cysteine from the N-terminus of the B chain, Sequences shown for Chain A are as follows: Insulin, SEQ ID NO:2; INSL3 (RLF), SEQ ID NO:3; INSL4, SEQ ID NO:4; INSL5, SEQ ID NO:5; INSL6 (RIF-1), SEQ ID NO:6; Relaxin 1, SEQ ID NO:7; Relaxin 2, SEQ ID NO:8; INSL7 (Relaxin 3), SEQ ID NO:9; IGF-1, SEQ ID NO: 10; and IGF-2, SEQ ID NO:11. Sequences shown for Chain B are as follows: Insulin, SEQ ID NO:12; INSL3 (RLF), SEQ ID NO:13; INSL4, SEQ ID NO:14; INSL5, SEQ ID NO:15; INSL6 (RIF-1), SEQ ID NO:16; Relaxin 1, SEQ ID NO:17; Relaxin 2, SEQ ID NO:18; INSL7 (Relaxin 3), SEQ ID NO:19; IGF-1, SEQ ID NO:20; and IGF-2, SEQ ID NO:21.

SEQUENCE LISTING

<160> NUMBER OF SEQ ID NOS: 21

Figure 2:
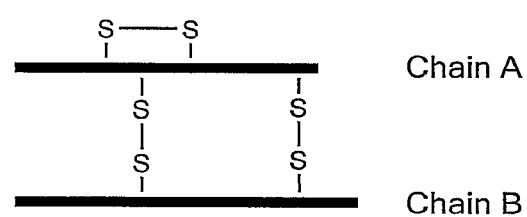
FIG. 2: Schematic representation of an Insulin like peptide. Bold lines represent a peptide chain. S represents a sulphur atom of a cysteine residue of the peptide and slim lines represent chemical bonds.
Figure 3:
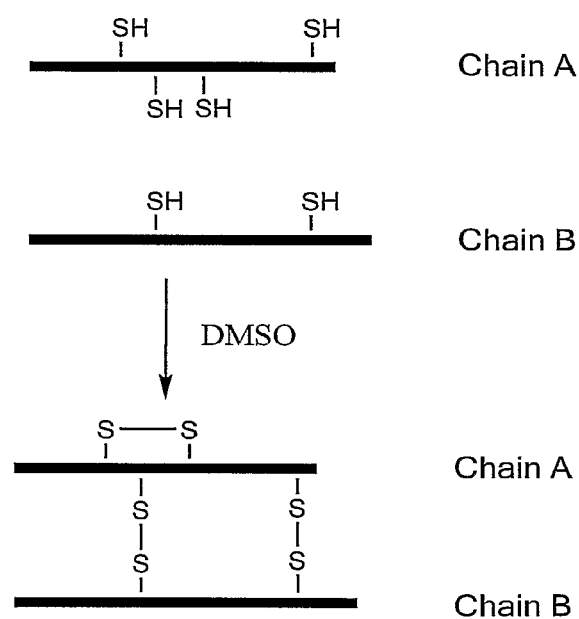
FIG. 3: Schematic representation of the preparation of Insulin like peptides by the random combination of linear chain A with linear chain B. Bold lines represent a peptide chain. S represents a sulphur atom of a cysteine residue of the peptide and slim lines represent chemical bonds.
Figure 4:
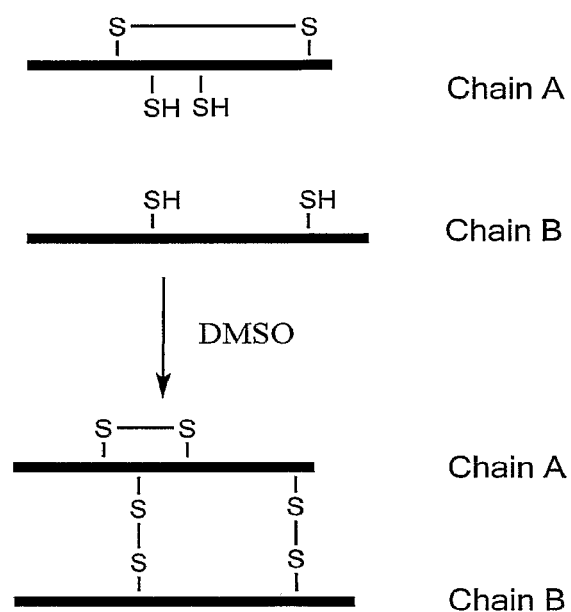
FIG. 4: Schematic representation of the preparation of Insulin like peptides by the random combination of monocyclic chain A with linear chain B. Bold lines represent a peptide chain. S represents a sulphur atom of a cysteine residue of the peptide and slim lines represent chemical bonds.
Figure 5:
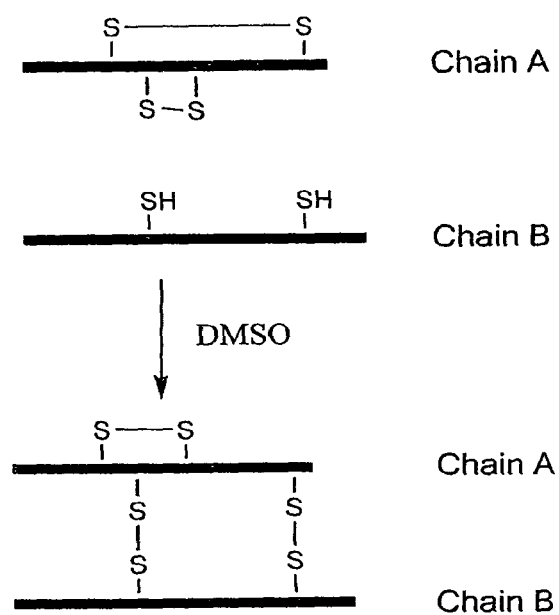
FIG. 5: Schematic representation of the preparation of Insulin like peptides by the random combination of bicyclic chain A with linear chain B. Bold lines represent a peptide chain. S represents a sulphur atom of a cysteine residue of the peptide and slim lines represent chemical bonds.
Figure 6:
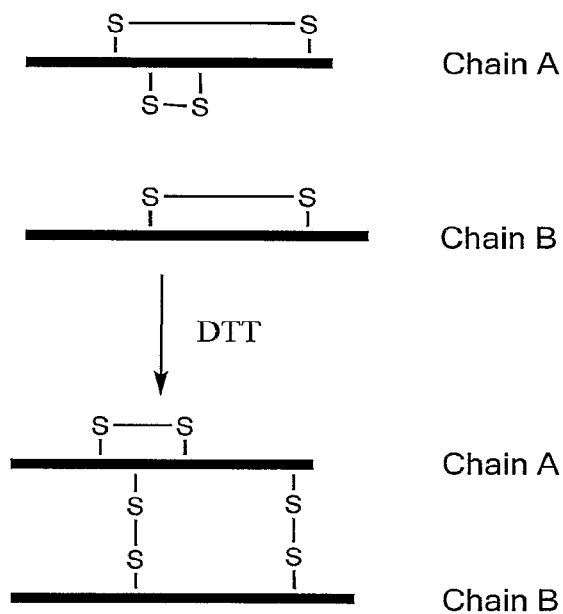
FIG. 6: Schematic representation of the preparation of Insulin like peptides by the random combination of bicyclic chain A with cyclic chain B. Bold lines represent a peptide chain. S represents a sulphur atom of a cysteine residue of the peptide and slim lines represent chemical bonds.
Figure 7:
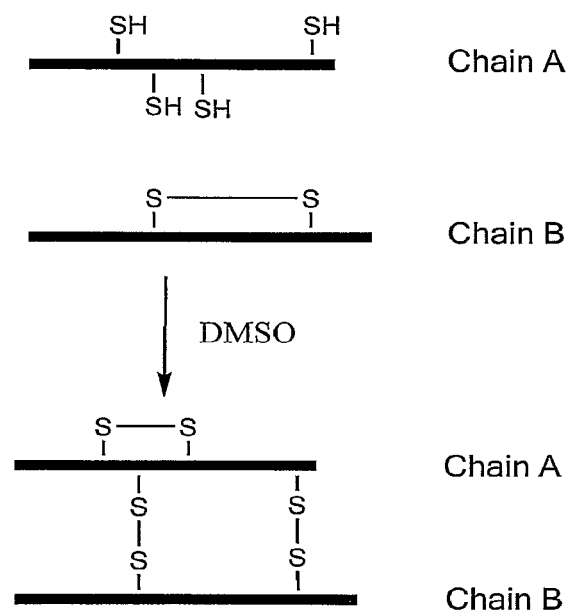
FIG. 7: Schematic representation of the preparation of Insulin like peptides by the random combination of linear chain A with cyclic chain B. Bold lines represent a peptide chain. S represents a sulphur atom of a cysteine residue of the peptide and slim lines represent chemical bonds.
Figure 8:
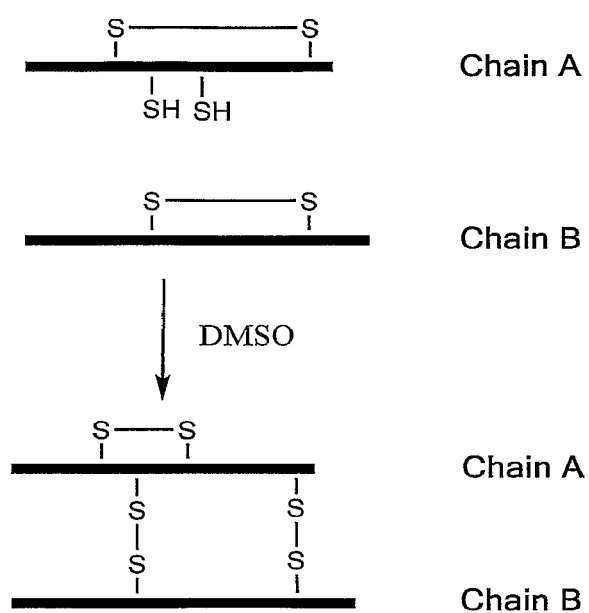
FIG. 8: Schematic representation of the preparation of Insulin like peptides by the random combination of monocyclic chain A with cyclic chain B. Bold lines represent a peptide chain. S represents a sulphur atom of a cysteine residue of the peptide and slim lines represent chemical bonds.
Figure 9:
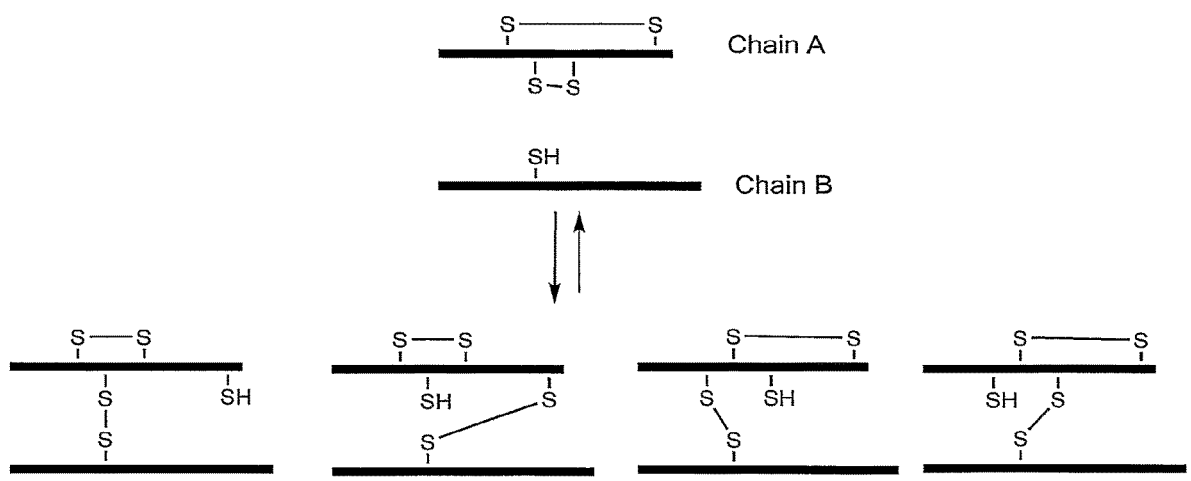
FIG. 9: Schematic representation of the combination of bicyclic peptides, which contain at least one cysteine residue. During the reaction up to four isomers can be formed. Bold lines represent a peptide chain. S represents a sulphur atom of a cysteine residue of the peptide and slim lines represent chemical bonds.

<210> SEQ ID NO 1
<211> LENGTH: 6
<212> TYPE: PRT
<213> ORGANISM: Artificial Sequence
<220> FEATURE:
<223> OTHER INFORMATION: Synthetic typical amino acid sequence
<220> FEATURE:
<221> NAME/KEY: MISC FEATURE
<222> LOCATION: (3)..(5)
<223> OTHER INFORMATION: Xaa may be natural or non natural amino acids.

<400> SEQUENCE: 1

Cys Cys Xaa Xaa Xaa Cys
1               5

<210> SEQ ID NO 2
<211> LENGTH: 21
<212> TYPE: PRT
<213> ORGANISM: Artificial Sequence
<220> FEATURE:
<223> OTHER INFORMATION: Insulin like peptide

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 26
<212> TYPE: PRT
<213> ORGANISM: Artificial Sequence
<220> FEATURE:
<223> OTHER INFORMATION: Insulin like peptide

<400> SEQUENCE: 3

Ala Ala Ala Thr Asn Pro Ala Arg Tyr Cys Cys Leu Ser Gly Cys Thr
1               5                   10                  15

Gln Gln Asp Leu Leu Thr Leu Cys Pro Tyr
            20                  25

<210> SEQ ID NO 4
<211> LENGTH: 25
<212> TYPE: PRT
<213> ORGANISM: Artificial Sequence
<220> FEATURE:
<223> OTHER INFORMATION: Insulin like peptide

<400> SEQUENCE: 4

Ser Gly Arg His Arg Phe Asp Pro Phe Cys Cys Glu Val Ile Cys Asp
1               5                   10                  15

Asp Gly Thr Ser Val Lys Leu Cys Thr
            20                  25

<210> SEQ ID NO 5
<211> LENGTH: 20
<212> TYPE: PRT
<213> ORGANISM: Artificial Sequence
<220> FEATURE:
<223> OTHER INFORMATION: Insulin like peptide

```
<400> SEQUENCE: 5

Asp Leu Gln Ala Leu Cys Cys Arg Glu Gly Cys Ser Met Lys Glu Leu
1               5                   10                  15

Ser Thr Leu Cys
            20

<210> SEQ ID NO 6
<211> LENGTH: 26
<212> TYPE: PRT
<213> ORGANISM: Artificial Sequence
<220> FEATURE:
<223> OTHER INFORMATION: Insulin like peptide

<400> SEQUENCE: 6

Gly Tyr Ser Glu Lys Cys Cys Leu Thr Gly Cys Thr Lys Glu Glu Leu
1               5                   10                  15

Ser Thr Ala Cys Leu Pro Tyr Ile Asp Phe
            20                  25

<210> SEQ ID NO 7
<211> LENGTH: 24
<212> TYPE: PRT
<213> ORGANISM: Artificial Sequence
<220> FEATURE:
<223> OTHER INFORMATION: Insulin like peptide

<400> SEQUENCE: 7

Arg Pro Tyr Val Ala Leu Phe Glu Lys Cys Cys Leu Ile Gly Cys Thr
1               5                   10                  15

Lys Arg Ser Leu Ala Lys Tyr Cys
            20

<210> SEQ ID NO 8
<211> LENGTH: 24
<212> TYPE: PRT
<213> ORGANISM: Artificial Sequence
<220> FEATURE:
<223> OTHER INFORMATION: Insulin like peptide
<220> FEATURE:
<221> NAME/KEY: MOD_RES
<222> LOCATION: (1)..(1)
<223> OTHER INFORMATION: The N-terminal Glu is pGlu or pyroglutamic acid
      (cyclized Glu).

<400> SEQUENCE: 8

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 9
<211> LENGTH: 24
<212> TYPE: PRT
<213> ORGANISM: Artificial Sequence
<220> FEATURE:
<223> OTHER INFORMATION: Insulin like peptide

<400> SEQUENCE: 9

Asp Val Leu Ala Gly Leu Ser Ser Cys Cys Lys Trp Gly Cys Ser
1               5                   10                  15

Lys Ser Glu Ile Ser Ser Leu Cys
            20
```

```
<210> SEQ ID NO 10
<211> LENGTH: 21
<212> TYPE: PRT
<213> ORGANISM: Artificial Sequence
<220> FEATURE:
<223> OTHER INFORMATION: Insulin like peptide

<400> SEQUENCE: 10

Gly Ile Val Asp Glu Cys Cys Phe Arg Ser Cys Asp Leu Arg Arg Leu
1               5                   10                  15

Glu Met Tyr Cys Ala
            20

<210> SEQ ID NO 11
<211> LENGTH: 21
<212> TYPE: PRT
<213> ORGANISM: Artificial Sequence
<220> FEATURE:
<223> OTHER INFORMATION: Insulin like peptide

<400> SEQUENCE: 11

Gly Ile Val Glu Glu Cys Cys Phe Arg Ser Cys Asp Leu Ala Leu Leu
1               5                   10                  15

Glu Thr Tyr Cys Ala
            20

<210> SEQ ID NO 12
<211> LENGTH: 30
<212> TYPE: PRT
<213> ORGANISM: Artificial Sequence
<220> FEATURE:
<223> OTHER INFORMATION: Insulin like peptide

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Insulin like peptide

<400> SEQUENCE: 13

Pro Thr Pro Glu Met Arg Glu Lys Leu Cys Gly His His Phe Val Arg
1               5                   10                  15

Ala Leu Val Arg Val Cys Gly Gly Pro Arg Trp Ser Thr Glu Ala
            20                  25                  30

<210> SEQ ID NO 14
<211> LENGTH: 41
<212> TYPE: PRT
<213> ORGANISM: Artificial Sequence
<220> FEATURE:
<223> OTHER INFORMATION: Insulin like peptide
<220> FEATURE:
<221> NAME/KEY: MOD_RES
<222> LOCATION: (1)..(1)
<223> OTHER INFORMATION: The N-terminal Glu is pGlu or pyroglutamic acid
      (cyclized Glu).
```

```
<400> SEQUENCE: 14

Glu Leu Leu Arg Glu Ser Leu Ala Ala Glu Leu Arg Gly Cys Gly Pro
1               5                   10                  15

Arg Phe Gly Lys His Leu Leu Ser Tyr Cys Pro Met Pro Glu Lys Thr
            20                  25                  30

Phe Thr Thr Thr Pro Gly Gly Trp Leu
            35                  40

<210> SEQ ID NO 15
<211> LENGTH: 25
<212> TYPE: PRT
<213> ORGANISM: Artificial Sequence
<220> FEATURE:
<223> OTHER INFORMATION: Insulin like peptide

<400> SEQUENCE: 15

Ser Arg Gln Thr Val Lys Leu Cys Gly Leu Asp Tyr Val Arg Thr Val
1               5                   10                  15

Ile Tyr Ile Cys Ala Ser Ser Arg Trp
            20                  25

<210> SEQ ID NO 16
<211> LENGTH: 34
<212> TYPE: PRT
<213> ORGANISM: Artificial Sequence
<220> FEATURE:
<223> OTHER INFORMATION: Insulin like peptide

<400> SEQUENCE: 16

Arg Glu Leu Ser Asp Ile Ser Ser Ala Arg Lys Leu Cys Gly Arg Tyr
1               5                   10                  15

Leu Val Lys Glu Ile Glu Lys Leu Cys Gly His Ala Asn Trp Ser Gln
            20                  25                  30

Phe Arg

<210> SEQ ID NO 17
<211> LENGTH: 28
<212> TYPE: PRT
<213> ORGANISM: Artificial Sequence
<220> FEATURE:
<223> OTHER INFORMATION: Insulin like peptide

<400> SEQUENCE: 17

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 18
<211> LENGTH: 29
<212> TYPE: PRT
<213> ORGANISM: Artificial Sequence
<220> FEATURE:
<223> OTHER INFORMATION: Insulin like peptide

<400> SEQUENCE: 18

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25
```

```
<210> SEQ ID NO 19
<211> LENGTH: 27
<212> TYPE: PRT
<213> ORGANISM: Artificial Sequence
<220> FEATURE:
<223> OTHER INFORMATION: Insulin like peptide

<400> SEQUENCE: 19

Arg Ala Ala Pro Tyr Gly Val Arg Leu Cys Gly Arg Glu Phe Ile Arg
1               5                   10                  15

Ala Val Ile Phe Thr Cys Gly Gly Ser Arg Trp
            20                  25

<210> SEQ ID NO 20
<211> LENGTH: 29
<212> TYPE: PRT
<213> ORGANISM: Artificial Sequence
<220> FEATURE:
<223> OTHER INFORMATION: Insulin like peptide

<400> SEQUENCE: 20

Gly Pro Glu Thr Leu Cys Gly Ala Glu Leu Val Asp Ala Leu Gln Phe
1               5                   10                  15

Val Cys Gly Asp Arg Gly Phe Thr Phe Asn Lys Pro Thr
            20                  25

<210> SEQ ID NO 21
<211> LENGTH: 32
<212> TYPE: PRT
<213> ORGANISM: Artificial Sequence
<220> FEATURE:
<223> OTHER INFORMATION: Insulin like peptide

<400> SEQUENCE: 21

Phe Tyr Arg Pro Ser Glu Thr Leu Cys Gly Gly Glu Leu Val Asp Thr
1               5                   10                  15

Leu Gln Phe Val Cys Gly Asp Arg Gly Phe Thr Phe Ser Arg Pro Ala
            20                  25                  30
```

The invention claimed is:

1. A method for making a chimeric polypeptide comprising two different peptide chains, wherein the two different peptide chains are chain A from one insulin like peptide and chain B from a different insulin like peptide, wherein chain A is selected from the A chain of insulin (INS), INSL3 (RLF), INSL4, INSL5, INSL6 (RIF-1), Relaxin 1 (RLN1), Relaxin 2 (RLN2), insulin-like growth factor 1 (IGF-1), and insulin-like growth factor 2 (IGF-2), and chain B is selected from the B chain of insulin (INS), INSL3 (RLF), INSL4, INSL5, INSL6 (RIF-1), Relaxin 1 (RLN1), Relaxin 2 (RLN2), insulin-like growth factor 1 (IGF-1), and insulin-like growth factor 2 (IGF-2); the method comprising
(i) combining a chain A which contains at least two disulfide bonds, with a chain B which contains at least one disulfide bond, in the presence of a reducing agent; or
(ii) combining a chain A which contains at least two disulfide bonds, with a chain B which contains at least two cysteine residues, in the presence of dimethyl sulfoxide (DMSO);
thereby making the chimeric polypeptide.

2. The method according to claim 1, wherein the chain A and the chain B are combined under conditions suitable to form (i) at least one intermolecular disulfide bond between the chain A and the chain B, and (ii) at least one additional intramolecular disulfide bond within at least one of the chain A and the chain B.

3. The method according to claim 1, further comprising esterifying a derivative of a natural or non-natural amino acid on a resin or on a trityl or benzhydryl linker, thereby forming an immobilized amino acid derivative; and sequentially reacting said immobilized amino acid derivative with optionally protected residues of insulin-like peptides on solid phase.

4. The method of claim 1, wherein the reducing agent is an organic thiol.

5. The method of claim 1, wherein the reducing agent is a linear chain A or chain B with free thiol groups.

6. A method for making a chimeric polypeptide comprising two different peptide chains, wherein the two different peptides are chain A from one insulin like peptide and chain B from a different insulin like peptide, wherein chain A is selected from the A chain of insulin (INS), INSL3 (RLF), INSL4, INSL5, INSL6 (RIF-1), Relaxin 1 (RLN1), Relaxin 2 (RLN2), insulin-like growth factor 1 (IGF-1), and insulin-like growth factor 2 (IGF-2), and chain B is selected from the B chain of insulin (INS), INSL3 (RLF), INSL4, INSL5, INSL6 (RIF-1), Relaxin 1 (RLN1), Relaxin 2 (RLN2), insulin-like growth factor 1 (IGF-1), and insulin-like growth factor 2 (IGF 2), the method comprising combining chain A which contains at least two disulfide bonds, with chain B in the presence of a reducing agent, thereby making the chimeric polypeptide.

7. The method of claim 6, wherein the reducing agent is an organic thiol.

8. The method of claim 6, wherein the reducing agent is a linear chain A or chain B with free thiol groups.

9. The method of claim 6, wherein the reducing agent is selected from reduced glutathione, cysteine, thiophenols, pyridinthiol, 3- or 5-nitropyridin-2-thiol, benzyl mercaptan, and dithiothreitol.

10. The method of claim 6, wherein the reducing agent is dithiothreitol.

11. The method of claim 6, wherein the chain A and the chain B are combined under conditions suitable to form (i) at least one intermolecular disulfide bond between the chain A and the chain B, and (ii) at least one additional intramolecular disulfide bond within at least one of the chain A and the chain B.

12. The method of claim 6, further comprising esterifying a derivative of a natural or non-natural amino acid on a resin or on a trityl or benzhydryl linker, thereby forming an immobilized amino acid derivative; and sequentially reacting said immobilized amino acid derivative with optionally protected residues of insulin-like peptides on solid phase.

* * * * *